United States Patent [19]

Ezer et al.

[11] 4,200,631

[45] Apr. 29, 1980

[54] TREATING MAMMALIAN SUBJECT SENSITIVE TO INDOMETHACIN ULCEROGENISIS

[75] Inventors: Elemer Ezer; Laszlo Szporny; Lilla Forgach; Eva Palosi; Eszter Cholnoky; Egon Karpati; György Hajós; Gyözö Hortobágyi; Katalin Gidai, all of Budapest, Hungary

[73] Assignee: Richter Gedeon Vegyeszeti Gyar Rt., Budapest, Hungary

[21] Appl. No.: 931,910

[22] Filed: Aug. 8, 1978

Related U.S. Application Data

[63] Continuation-in-part of Ser. No. 641,771, Dec. 17, 1975, abandoned.

[51] Int. Cl.$^2$ .................. A61K 31/62; A61K 31/405
[52] U.S. Cl. .................................... 424/232; 424/274

[58] Field of Search .......................... 424/231, 232

[56] References Cited

PUBLICATIONS

Hultmark et al.-Chem. Abst. vol. 83 (1975), p. 141,706k.
Gietka et al.-Chem. Abst. vol. 82 (1975), p. 291p.

*Primary Examiner*—Sam Rosen
*Attorney, Agent, or Firm*—Karl F. Ross

[57] ABSTRACT

Ulcer production in animals is prevented during prolonged antiphlogistic treatment with ulcerogenic quantities of indomethacin by using it in a composition of 1 part of indomethacin to 7.5 to 25 parts, preferably 10 parts by weight of a salicylate. Indomethacin is the most potent ulcerating compound among approved non-steroid antiinflammatory agents.

11 Claims, No Drawings

TREATING MAMMALIAN SUBJECT SENSITIVE TO INDOMETHACIN ULCEROGENISIS

CROSS REFERENCE TO RELATED APPLICATION

This application is a continuation-in-part of Ser. No. 641,771 filed Dec. 17, 1975, now abandoned.

FIELD OF THE INVENTION

This application relates to a method of attenuating the ulcerogenic effect of indomethacin in mammals subject thereto and requiring the indomethacin therapy for analgesic and antiphlogistic purposes. It also relates to a new pharmaceutical composition.

BACKGROUND OF THE INVENTION

As is known, all of the antiphlogistic agents hitherto used have the common disadvantage of causing gastrointestinal haemorrhages or ulcers. The ulcerogenic side-effects of 1-(chlorobenzoyl)5-methoxy-2-methyl-indole-3-yl-acetic acid (indomethacin), 4-butyl-1,2-diphenyl-pyrazolidine-3,5-dione (phenylbutazone) and acetylsalicylic acid have been reported in numerous publications (Bonfils et al: Bull. Mem. Soc. Med. Hosp. Paris, 5, 114 (1955); Somogyi et al: J. Pharm. Pharmacol. 21, 122 (1969); R. Nath: *Studies on the Pharmacology of Inflammation, M.D. Thesie Lucknow* University, Lucknow, India (1970)' Lee et al.: Arch. Int. Pharmacodyn. 19, 370 (1971); Bhargava et al.: European J. of Pharmacol. 22, 191 (1973); Katz et al.: Clin. Pharm. Ther. 6, 25 (1965); Leonard et al.: Clin. Pharmocol. Ther, 14, No. 1, 62 (1973).

Indomethacin is the most potent ulcerating compound among approved non-steroidal antiinflammatory agents. Its toxicity is directly related to its ulceration proclivities.

In prolonged treatments of various arthritic conditions two or more difficult antiphlogistic agents can sometimes be admininstered simultaneously to the patients. The antiphlogistic effects arising upon the simultaneous administration of indomethacin and acetylsalicyclic acid were investigated first in animal tests (Mielons et al.: J. Pharm. Pharmac. 20, 567 (1968); Swingle et al.: J. Pharmacol. Exp. Ther. 172, 423 (1970); Yesair et al.: Biochem. Pharm. 19, 1591 (1970). Since the oedema tests had not indicated the additivity of antiphlogistic effects, clinical tests were performed in order to elucidate this question (Champion et al.: Clin. Pharm. and Ther. 13, 239 (1972); Lindquist et al.: Clin. Pharm. and Ther. 15, 247 (1974). These clinical tests have shown that the blood indomethacin level is not affected by the simultaneous administration of acetylsalicylic acid, that is, these two types of antiphlogistic agents do not worsen the effects of one or the other.

OBJECT OF THE INVENTION

It is an object of the invention to provide an improved method of attenuating the ulcerogenic effects of antiphlogistic dosages of indomethacin and, more particularly, to provide an antiphlogistic method of treating animal subjects prone to ulcers upon indomethacin treatment to avoid the formation of such lesions.

SUMMARY OF THE INVENTION

We have found, most surprisingly, that when a dosage of indomethacin sufficient to induce ulcers in animals (but desirable for antiphlogistic purposes) is administered concurrently with a limited amount of an antiphlogistic salicylate (known to be ulcerogenic in its own right) the tendency to ulcer salt formation in the subjects is markedly reduced without any reduction in the antiphlogistic effect of the indomethacin. About 10 parts by weight of the salicylate per part by weight of the indomethacin are to be used for most effective results although less dramatic results obtain when 7.5 to 25 parts of the salicylate are used per part of indomethacin.

We have conducted, animal and human experiments aimed at investigating both the main antiphlogistic effect and the ulcerogenic side-effects appearing upon the administration of various combinations of antiphlogistic agents to the end of preparing a pharmaceutical composition in which the original antiphlogistic effects of the individual components are retained but the gastrointestinal side-effects are decreased to the minimum. The primary subjects of these experiments were the most widely applied antiphlogistic agents, i.e. the various salicylates (particularly acetylsalicylic acid) and indomethacin.

ANIMAL TESTS SERIES 1

The antiphlogistic effects were studied on Wistar rats of both sexes, animal subjects found to be particularly prone to indomethacin ulcerogenisis, each weighing 100 to 150 g. The animals were starved for 24 hours, and then 0.1 ml portions of a 1% carrageenin solution were injected under mild ether anaesthesia into the plantar region of one of the hind paws in order to provoke inflammation (oedema). The antiphlogistic agent or a combination thereof was introduced into the stomach of the animals via a stomach tube immediately before injecting the carrageenin solution. 4 hours after this treatment the animals were sacrificed, and both hind paws were amputated above the ankles. The paws were weighed, and the oedema weight was calculated from the weight difference of the treated and untreated paws.

The gastrointestinal ulcerogenic side-effects of the individual active agents and their combinations were also examined on Wistar rats weighing 100 to 150 g. The animals were starved for 24 hours, and the substances to be tested were administered to them via a stomach tube. 4 hours after the treatment the animals were sacrificed, the stomach was removed, incised along the greater curvature, washed, and the hemorrhages (brown spots) appearing on the glandular part were counted. The results were subjected to Student's "t"-test.

The ulcerogenic side-effects of several individual antiphlogistic agents were also examined by these tests. The results are summarized in Table 1. As will be apparent from the data of the Table 1, all the analgesic compounds examined possess more or less pronounced ulcerogenic side-effects.

Table 1

| Ulcerogenic side-effects of various antiphlogistic agents | | | | |
|---|---|---|---|---|
| | No. of test | Dosage mg/kg | No. of ulcer/ | Ulcer-free animals |
| Compound | animals | p.o. | stomach | No. | % |
| Indomethacin | 20 | 5 | 1.1 | 15 | 72 |
| Indomethacin | 28 | 10 | 6.5 | 5 | 18 |
| Indomethacin | 120 | 20 | 15.0 | 6 | 5 |
| Indomethacin | 41 | 30 | 24 | 0 | 0 |
| Niflumic acid | 18 | 12.5 | 0.6 | 14 | 78 |
| Niflumic acid | 16 | 25 | 10.2 | 2 | 12 |
| Niflumic acid | 15 | 50 | 19.0 | 0 | 0 |

Table 1-continued

Ulcerogenic side-effects of various antiphlogistic agents

| Compound | No. of test animals | Dosage mg/kg p.o. | No. of ulcer/ stomach | Ulcer-free animals No. | % |
|---|---|---|---|---|---|
| Niflumic acid | 15 | 100 | 23.0 | 0 | 0 |
| Phenylbutazone | 18 | 25 | 0.5 | 13 | 73 |
| Phenylbutazone | 16 | 50 | 0.6 | 4 | 25 |
| Phenylbutazone | 17 | 100 | 6.5 | 4 | 23 |
| Phenylbutazone | 15 | 200 | 20.0 | 1 | 7 |
| Aspirin | 25 | 25 | 4.7 | 2 | 8 |
| Aspirin | 25 | 50 | 5.4 | 3 | 10 |
| Aspirin | 120 | 100 | 6.5 | 18 | 14 |
| Aspirin | 58 | 400 | 11.0 | 7 | 12 |
| Sodium salicylate | 45 | 50 | 0.1 | 37 | 82 |
| Sodium salicylate | 28 | 100 | 0.1 | 27 | 96 |
| Sodium salicylate | 64 | 200 | 1.2 | 37 | 50 |
| Sodium salicylate | 45 | 400 | 1.1 | 32 | 71 |

The following tests aimed at investigating the effects which appear upon the administration of two different antiphlogistic agents in combination with each other. In the first tests combinations of indomethacin and sodium salicylate were studied. It has been found, unexpectedly, that these compounds mutually suppress the ulcerogenic side-effects of one anohter, while leaving the main antiphlogistic effects unchanged. This is indeed unpredictable since it is well known (See also Table 1 supra) that the above two compounds possess marked ulcerogenic side-effects when administered separately in therapeutic doseages.

In the tests the animals received the same dosages of indomethacin, and the amount of sodium salicylate administered was varied. We have found that the number of ulcer-free animals increases proportionally to the increase in the amount of sodium salicylate added, and when sodium salicylate is administered in a 20-fold amount with respect to indomethacin (10 ppw + 2 ppw: 1 ppw indomethacin, the ulcerogenic effect disappears completely, i.e. sodium salicylate antagonizes entirely the deleterious side-effect of indomethacin. Table 2 shows the ulcerogenic effects and Table 3 shows the antiphlogistic effects of combinations containing varying amounts of sodium salicylate besides indomethacin.

Table 2

Inhibition of indomethacin-induced ulcer by the simultaneous administration of sodium salicylate

| No. of animals tested | Dosage, mg/kg p.o. | | Ulcerogenic side-effects | | Ulcer-free animals | |
|---|---|---|---|---|---|---|
| | Indomethacin | Sodium Salicylate | No. of ulcer/stomach | Inhibition % | No. | % |
| 120 | 20 | — | $15.0 \pm 5^{xx}$ | — | 6 | 5 |
| 17 | 20 | 25 | $6.1 \pm 1.33^{xx}$ | $60^x$ | 2 | 12 |
| 18 | 20 | 50 | $7.5 \pm 1.4^{xx}$ | $50^x$ | 2 | 10 |
| 22 | 20 | 100 | $4.0 \pm 0.8^{xx}$ | $73^x$ | 3 | 13 |
| 58 | 20 | 200 | $0.27 \pm 0.1^{xx}$ | $98^x$ | 51 | 88 |
| 22 | 20 | 400 | 0 | $100^x$ | 22 | 100 |

$x = p\ 0.01$ (significance level determined by Student's "t"-test)
$xx$ = corrected with the mean standard error Table 3

Antiphlogistic effects of sodium salicylate, indomethacin and combinations thereof determined by carrageenin-oedema test

| Dosage of the compounds tested mg/kg p.o. | | No. of animals tested | Oedema-inhibiting effect % |
|---|---|---|---|
| sodium salicylate | indomethacin | | |
| 50 | — | 31 | 15 |
| 100 | — | 28 | $43^x$ |
| — | 5 | 21 | $40^x$ |
| — | 10 | 28 | $45^x$ |
| 50 | 5 | 29 | $40^x$ |
| 200 | 5 | 10 | $41^x$ |

In the following tests animals treated for 3 days with various combinations of indomethacin and sodium salicylate were examined. The non-starved test animals were treated orally for 3 days with compositions containing 20 mg/kg of indomethacin and increasing amounts of sodium salicylate. 73% of the animals receiving only indomethacin died on the 3rd day from peritonitis resulting from intestinal perforation, and clearly visible ulcers appeared in the intestines of the survivors. In contrast, when indomethacin was administered in combination with sodium salicylate, this severe side-effect could be antagonized completely. The results are summarized in Table 4.

Table 4

Antagonizing the gastrointestinal side-effect of indomethacin by sodium salicylate administered simultaneously (tests performed for 3 days on non-starved animals)

| No. of animals tested | Dosage mg/kg p.o. | | Died animals | | Ulcerous animals | |
|---|---|---|---|---|---|---|
| | Indomethacin | Sodium salicylate | No. | % | No. | % |
| 45 | 3 × 20 | — | 33 | 73 | 45 | 100 |
| 20 | 3 × 20 | 3 × 50 | 5 | 25 | 11 | 55 |
| 20 | 3 × 20 | 3 × 100 | 3 | 15 | 3 | 15 |
| 45 | 3 × 20 | 3 × 200 | 0 | 0 | 0 | 0 |

It has also been studied whether sodium salicylate also antagonizes the ulcerogenic side-effects of antiphlogistic agents other than indomethacin. These tests have shown that the ulcerogenic side-effects of phenylbutazone, nifluminic acid and acetylsalicylate acid or its salt can also be antagonized effectively by administering them together with sodium salicylate, and the main antiphlogistic effects of these compounds remain unchanged, or even the antiphlogistic effects of the two active agents are superimposed.

SERIES 1 DISCUSSION

The results listed above prove unambiguously that sodium salicylate antagonizes the gastrointestinal hemmorhagic or ulcerogenic side-effects of other non-steroidal antiphlogistic agents and specifically indomethacin, without affecting the main antiphlogistic effect of either the indomethacin or the salicylate. Similarly effects are shown by compositions which contain other salicylate acid salts, or in certain cases even salicylate acid itself, instead of sodium salicylate.

Thus the invention relates to pharmaceutical compositions containing as active agent a non-steroidal antiphlogistic substance or a pharmaceutically acceptable salt thereof and salicylic acid or an alkali salicylate (as the salicylate) in a weight ratio of about 20:1 optionally together with another biological substance or a carrier or diluents.

As the alkali salicylate preferably sodium or lithium salicylate is employed.

ANIMAL TESTS-SERIES 2

Materials and Methods

Indomethacin and Na-salicylate of approved grades were obtained.

Acute toxicity ($LD_{50}$)

Rq: WISTAR rats of both sexes, weighing 180-200 g, were used. Compounds were administered by gauge in suspension prepared with Tween-80. Respective $LD_{50}$s were determined by probit analysis.

Analgesic effect (writhing)

The analgesic effect was studied on rates of both sexes, weighing 130-150 g, according to Sigmund, E., Cadmus, R. and Go Lu: Proc. Soc. exp. Biol. Med. 95, 729 (1957). Writhing syndrome was induced with 1 ml of 0.02% phenyl-p-benzoquinone per 100 g body weight i.p. 30 minutes prior to treatment with the test compound.

Antipyretic effect 1 ml/100 g of a 20% suspension of yeast was injected s.c. according to Winder, C. V., Wax, J., Scotti, L., Schesser, R., Jones, E. and Schort, F.: J. Pharmac. Exp. Ther. 138, 405 (1962) to starved but watered animals. Sixteen hours following injection of yeast, rectal temperature was recorded by an Ellab thermometer, the animals then received the test compound and their body temperature was recorded for another 6 hours.

Carrageenin oedema

Groups comprising 10 male Rg: WISTAR rats each, weighing 150-200 g were used. Foot oedema was induced according to Winter, C. A., Risley, E. A. and Nuss, G. W.: J. Pharmac. Exp. Ther. 141, 369, 375 (1963) by 0.1 ml of 2% carrageenin solution injected into the plantar region. Test compounds were administered p.o. 120 minutes prior to carrageenin injection. Development of the oedema by volumetric changes were followed 30 minutes and 3 hours after the challenging injection.

Adjuvant polyarthritis

Groups comprising 10 male Rg: WISTAR rats, weighing 130-150 g were used to induce adjuvant polyarthritis according to Newbold, R. B.: Brit. J. Pharm. 21, 127 (1963). The rats received a sub-plantar injection of 5 mg/ml killed Mycobacterium butyricum suspended in liquid paraffin in the left hindleg, each animal was injected with 0.05 ml. The test compounds were administered p.o. one day prior to the injection with the Mycobacterium butyricum. Primary reaction was determined on the treated extremity at 3-day intervals for 21 days, secondary reaction on the untreated foot from the 10th until the 21st day after injection.

Intestinal ulceration

Unfasting female rats, weighing 120-150 g were treated p.o. with the test compounds. Intestinal ulceration was determined according to our own method by inflation (Ezer, E. and Szporny, L.: J. Pharm. Pharmac. 27, 866-867 (1975). It had been proved that intestinal bursting pressure had been reduced by ulceration. Intestinal bursting pressure was determined 24 and 48 hours after administration of test compounds and expressed as mmHg. The method is carried out as follows: the whole intestinal tract from the pylorus to the coecal orifice is cautiously removed after binding off one end. A polyethylene cannula is introduced into the other end and joined to a mercury manometer and to a 3-valve Griffin rubber ball. The intestinal tract is immersed into physiological saline maintained at 37° C. Intraintestinal pressure is increased by inflation until air bubbles indicate perforation at any part. This pressure is regarded as a characteristic of the bursting strength of the intestinal wall and is expressed in mmHg.

Gastric ulceration

Gastric ulceration was studied according to Lee, Y. H., Mallison, K. and Cheng, W. D.: Arch. int. Pharmacodyn. 19, 370-377 (1971) on female rats, weighing 120-150 g, fasted for 24 hours. Four hours following oral treatment the animals were killed by ether inhalation, stomachs were excised and cut along the large curvature, lightly washed and brown patches on the glandular surface were counted.

Determination of indomethacin level in serum

Serum levels of indomethacin were determined from blood samples collected from the carotid artery after transsection of the artery 15, 30, 60, 120, 180 and 240 minutes after treatment. Indomethacin concentrations were determined according to Hucker, H. B., Zacchei, A. G., Cox, S. D., Brodie, D. A. and Cantwell, N. H. R: J. Pharmac. Exp. Ther. 153, 237-250 (1966) by spectrofluorometry following extraction with alkaline heptane. Results were evaluated by Student's t-test.

Results

The acute toxicity of indomethacin alone was 72-fold of that administered in combination with Na-salicylate (Table 5), a remarkable reduction in favor of the combined preparation.

The antipyretic effects are presented in FIG. 1. Effect of the combined preparation developed quicker and was more pronounced than that of either parent compound alone.

Analgesic $ED_{50}$ obtained in writhing tests are described in Table 6.

Antiinflammatory effects achieved in Carrageenin oedema are summarized in Table 7. These effects are unambiguous, $ED_{50}$ of indomethacin alone was 2.4 ml/kg, for the combined preparation was 11 mg/kg (corresponding to 1.1 mg/kg indomethacin content).

Data of Table 8 indicated that the combined preparation was highly affective in adjuvant polyarthritis test as well.

Results of acute (4 hour) gastric ulceration are summarized in Table 9. Number of ulcers were increased and number of animals devoid of ulcers was reduced by indomethacin, tthis effect showed dose-dependence $UD_{50}$, the median dose inducing ulceration was 5 mg/kg p.o. for indomethacin alone, and exceeding 600 mg/kg for the combined preparation because 90% of the animals treated with this dose were devoid of ulcers. Indomethacin is the most potent ulcerating compound among non-steroid antiinflammatory agents. As a matter of fact the toxicity of indomethacin is directly related to gastrointestinal ulceration.

The intestinal bursting pressure 48 hours after various treatments are recorded in Table 10. The dose lowering intestinal bursting pressure to 50 mmHg was calculated from the dose-effect curves and designated as $IUD_{50}$, this was 14 mg/kg for indomethacin alone and 1750 mg/kg for the combined preparation, a 125-fold ratio in favor of the combined preparation.

Pharmacological effectivity was related to intestinal toxicity in Table 11. Therapeutical index ($LD_{50}/ED_{50}$) and that related to intestinal toxicity ($IUD_{50}/ED_{50}$) were increased in the combination preparation.

Serum levels of indomethacin are presented in Table 12. No difference of serum levels were found between the low dose groups treated with 2.5 mg/kg indomethacin alone vs that treated with 2.5 mg/kg indomethacin+25 mg/kg Na-salicylate, or 5 mg/kg indomethacin vs 5 mg/kg indomethacin+50 mg/kg Na-salicylate, respectively. However, serum levels of the group treated with the high dose of the combined preparation (20 mg/kg indomethacin+200 mg/kg Na-salicylate) were depressed in comparison to those treated with 20 mg/kg indomethacin alone.

SERIES 2 DISCUSSION

The specific antiinflammatory activity of indomethacin is the most favorable in the group of non-steroid antiinflammatory agents. However, this favorable effect is accompanied by strongly associated gastrointestinal side effects. The above tests indicate that the gastrointestinal effects of indomethacin can be eliminated when administered with Na-salicylate in a ratio of 1:10.

The pharmacological parameters of this combination are more favorable than those of indomethacin alone. This interaction results in a low toxicity and low degree and low incidence of gastrointestinal side effects.

The threapeutic index of the combination is increased by orders of magnitude in two antiinflammatory tests, while that in the analgesic test is unaffected.

The antipyretic effect of the combined preparation is more pronounced, although shorter than that of the parent compounds.

First of all there is the possibility of depressed indomethacin blood levels after combined treatment. According to Yesair, D. W., Callahan, M., Remington, L. and Kansler, C. J.: Biochem. Pharmacol., 19, 1591–1600 (1970) indomethacin blood levels of rats were reduced by 30–50% when treated subsequently with Na-salicylate. These studies were followed by several clinical investigations. In the course of these studies the patients received indomethacin and aspirin and their indomethacin blood levels were determined [Champion, G. D., Paulus, H. E., Mongan, E., Okun, R., Pearson, C. M. and Sarkissian, E.: Clin. Pharmacol. Ther., 13, 239–244 (1972); Lindquist, B., Jensen, K. M., Johansson, H. and Hansen, T.: Clin. Pharmacol. Ther., 15, 247–252 (1974); Kaldestad, E., Hansen, T. and Brath, H. K.: Europ. J. Clin. Pharmacol., 9, 199–207 (1975); Brooks, P. M., Walker, J. J., Bell, M. A., Buchanan, W. W. and Rhymer, A. R.: Brit. Med. J., 113, 69–71 (1975)]. The reported results were contradictory. Some authors found lower blood levels, others did not find such lowering.

In our tests on rats, lower doses up to 50 mg/kg did not depress indomethacin levels in blood while high doses of 200 mg/kg did. However, the more favorable pharmacological results with the combinations appear unrelated to actual blood levels of indomethacin [Torgyan, S., Ady, E., Wagner, L., Neumann, T. and Ezer, E.: 10th International Congress of Gastroenterology, Budapest, June 23–29 Abstr. (1976); Ezer, E., Palosi, E., Jajos, Gy. and Szporny, L.: J. Pharm. Pharmac., 28, 655 (1976a); Ezer, E., Palosi, E., Hajos, Gy. and Szporny, L.: Progress in Peptic Ulcer (1967b), Budapest Publishing House of the Hungarian Academy of Sciences].

Aspirin-like non-steroid antiinflammatory agents, except Na-salicylate, are potent inhibitors of prostaglandin synthesis [Vane, J. R.: Nature New Biology, 231, 232–236 (1971)], the most potent one being indomethacin. It has been assumed by some authors [Vane, ibid and Robert, A.: Prostaglandin, 6, 523–532 (1974)] that gastrointestinal side effects of non-steroid antiinflammatory agents are attributable to local prostaglandin deficiency.

According to Smith, M. J., Ford-Hutchinson, A. W. and Elliott, P. N.: J. Pharm. Pharmac., 21, 122–124 (1975) Na-salicylate and aspirin have similar antiinflammatory potency in animal experiments, although Na-salicylate is practically ineffective as a prostaglandin inhibitor.

An assumption that can be derived is that beside the importance of absolute amounts of prostaglandin, their balanced ratio might be equally important for gastrointestinal protection, and that ulceration is inhibited because of the maintained equilibrium due to the presence of Na-salicylate.

TABLE 5

| COMPOUND | LD$_{50}$-s on rats LD$_{50}$ mg/kg p. o. |
|---|---|
| Na-salicylate | 2404.0 |
| Indomethacin | 12.5 |
| Combined preparation | 907.0 |

TABLE 6

| COMPOUND | Analgesic effect on rats ED$_{50}$ mg/kg p. o. |
|---|---|
| Indomethacin | 3.65 |
| Na-salicylate | 513.00 |
| Combined preparation | 275.00 |

TABLE 7

Antiinflammatory effect of Na-salicylate, indomethacin and the combined preparation in Carrageenin oedema expressed in percentage of control

| TREATMENT - 2 HOURS PRIOR TO CARRAGEENIN | NUMBER OF ANIMALS | DOSE MG/KG P.O. | INHIBITION OF OEDEMA FOLLOWING ADMINISTRATION OF CARRAGEENIN | | ED$_{50}$ MG/KG AT 180 MIN. |
|---|---|---|---|---|---|
| | | | 30 MIN. | 180 MIN. | |
| Na-salicylate | 10 | 50 | 10.6 | 11.7 | |
| | 9 | 100 | 7.3 | 22.8 | 320 |
| | 10 | 200 | 19.3 | 31.3 | |
| Indomethacin | 10 | 1.25 | 23.6 | 30.5 | |
| | 10 | 2.50 | 42.3 | 53.0 | 2.4 |
| | 10 | 5.00 | 42.7 | 53.4 | |
| Combined Preparation | 10 | 6.25 | 3.3 | 6.5 | |
| | 10 | 12.50 | 34.7 | 53.6 | 11 |
| | 10 | 25.00 | 46.0 | 52.6 | |

TABLE 8

Antiinflammatory effect of indomethacin and the combined preparation in adjuvant polyarthritis expressed in percentage of control

| TREATMENT | NUMBER OF ANIMALS | DAILY DOSE MG/KG P.O. | INHIBITION OF OEDEMA 3rd DAY LEFT* | 21st DAY LEFT | 21st DAY RIGHT | $ED_{50}$ 21st DAY LEFT | $ED_{50}$ 21st DAY RIGHT |
|---|---|---|---|---|---|---|---|
| Indomethacin | 12 | 0.65 | 26.7 | 46.6 | 47.2 | 1.4 | 0.9 |
|  | 12 | 1.25 | 36.3 | 45.7 | 35.6 |  |  |
|  | 12 | 2.50 | 36.8 | 58.0 | 72.6 |  |  |
| Combined preparation | 12 | 6.50 | 40.0 | 49.8 | 53.7 | 8.0 | 5.5 |
|  | 12 | 12.50 | 37.1 | 52.0 | 42.7 |  |  |
|  | 12 | 25.00 | 42.4 | 59.7 | 61.6 |  |  |

* = challenged foot (primary effect)

TABLE 9

Prevention of gastric ulceration induced by indomethacin after combined treatment

| TREATMENT | NUMBER OF RATS | DOSE MG/KG P.O. | NUMBER OF ULCERS/RAT | INHIBITION OF ULCER % | PERCENTAGE OF ANIMALS WITHOUT ULCERS |
|---|---|---|---|---|---|
| Indomethacin | 10 | 2.5 | 3.1 ± 1.5 | — | 78 |
|  | 20 | 5.0 | 6.3 ± 2.4 | — | 50 |
|  | 28 | 10.0 | 11.2 ± 1.5 | — | 18 |
|  | 120 | 20.0 | 15.9 ± 1.1 | — | 5 |
| Indomethacin + Na-salicylate | 18 | 20 + 50 | 7.5 ± 1.4* | 52 | 5 |
|  | 22 | 20 + 100 | 4.0 ± 0.8* | 75 | 15 |
|  | 58 | 20 + 200 | 0.3 ± 0.1* | 98 | 88 |
| Combined preparation 1:10 | 10 | 600 | 0.6 ± 0.3* | 97 | 90 |

* = difference in comparison to 20 mg/kg indomethacin alone statistically significant ($P < 0.01$)

TABLE 10

Intestinal ulceration in rats treated with indomethacin alone or in combination

| TREATMENT | NUMBER OF ANIMALS | DOSE MG/KG P.O. | BURSTING PRESSURE (mmHg) - 48 HOURS AFTER TREATMENT; MEANS ± S. E. | $IUD_{50}$ |
|---|---|---|---|---|
| Untreated | 24 | — | 160 ± 4.2 | — |
| Indomethacin | 10 | 10 | 72 ± 16.1* |  |
|  | 10 | 15 | 35 ± 10.9* | 14 |
|  | 10 | 20 | 31 ± 12.8* |  |
| Combined preparation | 10 | 220 | 178 ± 4.8 |  |
|  | 10 | 500 | 116 ± 12.0 | 1750 |
|  | 10 | 750 | 114 ± 14.0 |  |
|  | 20 | 900 | 74 ± 12.0* |  |
|  | 10 | 1200 | 82 ± 16.0* |  |
|  | 10 | 1500 | 82 ± 17.0* |  |

* = $P < 0.01$

TABLE 11

Therapeutical index and relative intestinal toxicity of parent compounds alone and in combination; A - in Carrageenin oedema, B - in adjuvant polyarthritis; C - in phenylbutazoquinone writhing test.

| TREATMENT | THERAPEUTICAL INDEX $LD_{50}/ED_{50}$ A | B | C | RELATIVE INTESTINAL TOXICITY $IUD_{50}/ED_{50}$ A | B | C |
|---|---|---|---|---|---|---|
| Indomethacin | 5.2 | 8.9 | 3.4 | 5.8 | 10.0 | 3.8 |
| Combined preparation | 82.0 | 113.0 | 3.3 | 159.0 | 218.0 | 6.3 |
| Na-salicylate | 7.5 | — | 4.6 | — | — | — |

TABLE 12

Serum levels of indomethacin in rats following treatment with indomethacin alone or in combination

| TREATMENT | NUMBER OF RATS | DOSE MG/KG P.O. | SERUM LEVELS OF INDOMETHACIN (mg/ml) AFTER THE TREATMENT 15 | 30 | 60 | 120 | 180 | 240 (MIN.) |
|---|---|---|---|---|---|---|---|---|
| Indomethacin | 5 | 2.5 | 4.1 ± 0.4 | 5.6 ± 0.3 | 4.1 ± 0.2 | 6.9 ± 0.7 | 5.5 ± 0.2 | 5.1 ± 0.2 |
|  | 5 | 5.0 | 6.9 ± 1.2 | 9.2 ± 0.2 | 7.4 ± 0.2 | 13.0 ± 1.0 | 12.5 ± 0.7 | 9.8 ± 0.5 |
|  | 5 | 10.0 | — | 43.0 ± 0.8 | 37.2 ± 6.1 | 45.2 ± 3.7 | 29.3 ± 1.7 | 31.7 ± 3.0 |
|  | 5 | 20.0 | 30.2 ± 2.1 | 36.9 ± 1.4 | 38.9 ± 2.6 | 75.4 ± 4.0 | 66.9 ± 5.1 | 70.7 ± 4.1 |
| Indomethacin + Na-salicylate | 5 | 2.5 + 25 | 4.1 ± 0.4 | 4.3 ± 0.3 | 4.1 ± 0.3 | 6.3 ± 0.6 | 4.5 ± 0.6 | 4.4 ± 0.4 |

TABLE 12.-continued

Serum levels of indomethacin in rats following treatment with indomethacin alone or in combination

| TREATMENT | NUMBER OF RATS | DOSE MG/KG P.O. | SERUM LEVELS OF INDOMETHACIN (mg/ml) AFTER THE TREATMENT | | | | | |
|---|---|---|---|---|---|---|---|---|
| | | | 15 | 30 | 60 | 120 | 180 | 240 (MIN.) |
| | 5 | 5.0 ± 50 | 7.7 ± 0.8 | 5.5 ± 1.0 | 9.2 ± 0.8 | 10.3 ± 0.4 | 8.7 ± 0.4 | 6.3 ± 0.8 |
| | 5 | 10.0 ± 100 | — | 16.0 ± 4.8* | 19.0 ± 3.3* | 16.2 ± 1.9* | 16.2 ± 1.2* | 14.4 ± 1.2* |
| | 5 | 20.0 ± 200 | 11.7 ± 1.4* | 9.3 ± 1.4* | 14.1 ± 1.4* | 22.7 ± 3.5* | 20.9 ± 2.0* | 15.6 ± 4.8* |

* = differences between indomethacin alone and in combination within respective doses of indomethacin are statistically significant (P = 0.1)

HUMAN TEST—ANIMAL-HUMAN CORRELATION—BLOOD LOSS TESTS

Patients and Methods

A modified method (Leonards, J. R., Levy, G.: Clin. Pharmacol. and Ther., 1969, 10, 571; Leonards, J. R., Levy, S.: Clin. Pharmacol. and Ther., 1973, 14, 62; Philips, B., Kraus, P. J., Ahlen, J. L., Buslee, R.: Toxicol. and Appl. Pharmacol., 1971, 20, 515) employing $Cr^{51}$ labeled erythrocytes was tested on healthy human subjects (ages between 18 and 70 years) who had apparently no gastrointestinal, hematological and rheumatic dosorders. Following administration of $Cr^{51}$ labeled erythrocytes, stool was collected for 3 days regarded as control period, then subjects were treated with doses of indomethacin, aspirin, phenylbutazone, Na-salicylate and indomethacin + Na-salicylate, respectively, as described in Table 13. Total daily doses wer consumed in three fractions, treatment continued for another 3 days during which stool was collected.

Long-term treatment (for 4 weeks) with indomethacin and indomethacin + Na-salicylate was applied to patients of both sexes (ages between 30 and 70 years) who has some rheumatic disease history for 1 to 8 years. One week prior to experimental treatment all other antiinflammatory compounds had been withdrawn. Total daily doses as described in Table 14 were provided in 3×1 capsules. Each group comprised 20 patients, $Cr^{51}$ labeling was performed 4 days before the end of the 4th week of treatment, stool was collected for the last 4 days of the treatment. Patients were requested to report about subjective symptoms at weekly intervals.

The $Cr^{51}$ labeled erythrocyte modified method (Torgyan, S., Ady, E., Wagner, L., Neumann, T., Ezer, E.: 10th International Congress of Gastroenterology, 1976, Budapest, Abs. vol. 1, 349; Torgyan, S., Ady, E., Wagner, L., Neumann, T., Balogh, K., Ezer, E.: Magyar Belorv. Arch. Suppl., 1976, 12, 116), used to establish daily gastrointestinal blood loss. Erythrocytes were radio-labeled as in the case for determination of circulatory blood volume or for that of erythrocyte half life. The stool radioactivity was determined after incineration of samples to ashes, since this method is more reliable than homogenization and dilution. Gastrointestinal blood loss was expressed in ml as the quotient of radioactivity in stool and blood samples. Results were evaluated by Student's t-test.

Results

Average of spontaneous gastrointestinal blood loss in healthy subjects in 0.56 ml (Table 13). Blood loss after treatment with various non-steroidal antiinflammatory compounds was significantly increased, except after treatment with Na-salicylate. These results are consistent with those described by various authors (Leonards et al, supra). The combined treatment with indomethacin + Na-salicylate caused significantly reduced blood loss in comparison to treatment with indomethacin alone.

Observations on gastrointestinal blood loss at the end of long-term treatment with indomethacin + Na-salicylate and with indomethacin alone are summarized in Table 14. The gastrointestinal blood loss after the combined composition treatment was unambiguously less in comparison to monotherapy with indomethacin. Also, subjective symptoms were reduced by combined treatment, and reported pain and morning rigidity of the limbs was milder. In two cases burning sensations in the stomach occurred as side effect. No unfavorable side effect was observed in laboratory findings, i.e. blood cell sedimentation rate, hematological values, liver function tests, SGPT, SGOT enzyme activity.

TABLE 13.

Gastrointestinal blood loss in healthy subjects following treatment with various antiinflammatory compounds

| TREAEMENT | NUMBER OF SUBJECTS | TOTAL DAILY DOSE, MG P.O. | GROUP DESIGNATION | MEAN DAILY BLOOD LOSS (ML) ± S.D. | STATISTICAL SIGNIFICANCE | |
|---|---|---|---|---|---|---|
| Control | 40 | — | A | 0.56 ± 0.4 | — | |
| Na-salicylate (S.S.) | 5 | 3000 | B | 1.16 ± 1.8 | A - B | N.S. |
| Aspirin | 7 | 3000 | C | 1.50 ± 0.5 | A - C | p < 0.01 |
| Phenylbutazone | 4 | 600 | D | 1.45 ± 0.7 | A - D | p < 0.1 |
| Indomethacin (Ind.) | 6 | 150 | E | 2.75 ± 1.3 | A - E | p < 0.01 |
| Ind. + S.S.* | 9 | 150 ± 1500 | F | 1.35 ± 0.9 | A - F | p < 0.01 |
| | | | | | F - E | p < 0.01 |

*. Preparation made by Gedeon Richter, Budapest, Hungary

TABLE 14.

Gastrointestinal blood loss at the end of 4-week treatment with indomethacin alone and combined treatment with indomethacin + Na-salicylate

| TREATMENT | NUMBER OF SUBJECTS | TOTAL DAILY DOSE, MG P.O | GROUP DESIGNATION | MEAN DAILY BLOOD LOSS (ML) ± S.D. | STATISTICAL SIGNIFICANCE |
|---|---|---|---|---|---|
| Control | 33 | — | A | 0.58 ± 0.78 | |

TABLE 14.-continued

Gastrointestinal blood loss at the end of 4-week treatment with indomethacin alone and combined treatment with indomethacin + Na-salicylate

| TREATMENT | NUMBER OF SUBJECTS | TOTAL DAILY DOSE, MG P.O. | GROUP DESIGNATION | MEAN DAILY BLOOD LOSS (ML) ± S.D. | STATISTICAL SIGNIFICANCE | |
|---|---|---|---|---|---|---|
| Indomethacin | 20 | 75 | B | 3.30 ± 0.79 | A - B | $p < 0.01$ |
| Indomethacin + Na-salicylate | 20 | 75 + 750 | C | 1.12 ± 0.71 | A - C | $p < 0.01$ |

CONCLUSION

Results of animal experiments performed by Ezer, E., Palosi, E., Hajos, Gy. and Szporny, L.: J. Pharm. Pharmac., 1976, 28, 655; Ezer, E., Palosi, E., Hajos, Gy. and Szporny, L.: Progress in Peptic Ulcer Eds: Gy. Mozsik and T. Javor Publishing House of the Hungarian Academy of Sciences, 1976, Budapest; Ezer, E., Palosi, E., Hajos, Gy. and Szporny, L.: J. Pharm. Pharmac., in press; were confirmed in human therapy, that is adverse gastrointestinal side effects of indomethacin were markedly reduced by combining it with Na-salicylate. Since both indomethacin and Na-salicylate are widely but separately used antirheumatic agents, a combined preparation is advantageous over their separate administration.

The above compositions can be prepared by methods commonly applied in the pharmaceutical industry. The pharmaceutical compositions can be presented, e.g. in the form of tablets, sugar- or film-coated tablets, capsules, suppositories, injectable solutions, etc.

The pharmaceutical compositions according to the invention can be administered orally, rectally and/or parenterally either in a single dosage or in subdivided forms. For oral administration the compositions are presented preferably in the form of tablets, sugar- or film-coated tablets or capsules. Film-coated tablets are particularly preferable unit dosage forms. These orally administerable compositions contain generally no filler, but in some cases conventional filling agents, e.g. lactose or starch can also be admixed. As binding or granulating agent, e.g. gelatin, sodium carboxymethylcellulose, methylcellulose, polyvinylpyrrolidine or gellified starch can be used. The most appropriate disintegrating agents are potato starch and microcrystalline cellulose, but other disintegrating agents, such as ultraamylopectin, formaldehyde-casein condensates, etc. can be used as well. As lubricating and antiadhesive substances, e.g. talc, colloidal silicic acid, stearine, calcium or magnesium stearate, etc. can be used.

The tablets can be prepared, e.g. by conventional wet granulation-compression method. In this instance a dry blend of the active agents, fillers and optionally a part of this disintegrating agents is kneaded with an aqueous, alcoholic or aqueous-alcoholic solution of the appropriate binding agent, the mass is granulated, and the obtained granules are dried. Thereafter the other additives (e.g. the remaining part of the disintegrating agents, lubricants, antiadhesive substances, etc.) are blended with the granular substance, and the blend is compressed into tablets. If desired, the tablets can be provided with parting incisions in order to facilitate their division at administration. If desired, the tablets can be film-coated with substances resistant towards gastric juice, such as shellac, cellulose-acetate phthalate or Eudragit-L ®. These film-formng substances are usually deposited onto the tablet from an alcohol, particularly isopropanol solution.

From the appropriate combinations of the active agents and additives the tablets can also be prepared by a direct pressing method and, if desired, the resulting tablets can be provided with an enteric coating.

If desired, the tablets can be coated with conventional protecting, flavoring and/or coloring agents such as sugar, cellulose derivatives (methyl or ethylcellulose, sodium carboxymethylcellulose, etc.), polyvinylpyrrolidine, calcium phosphate, calcium carbonate, coloring agents and varnishes commonly used in the food and pharmaceutical industry, iron oxide pigments, aroma substances, etc. For the sake of convenience the thus-ontained coated tablets are referred to in the specification and claims as "sugar-coated tablets", with the understanding that this term also covers coated tablets which contain no sugar in the coating layer.

Capsules are prepared by filling the mixture of the active agents into hard gelatin capsules, or coating preformed pellets of the dried materials with soft gelatin.

Compositions for rectal administration are presented in the form of suppositories. The suppositories contain, besides the active agents, conventional carriers, such as vegetable fats (e.g. hardened vegetable oils) or triglycerides of $C_{12-18}$ fatty acids. Witepsol ® proved to be a particularly preferable carrier for the preparation of suppositories. The active agents are homogenized with the molten carrier, and the mass is cast into suppository molds.

Compositions for parenteral administration are presented in injectable forms. To prepare injectable solutions the active agents are dissolved, e.g. in distilled water and/or various organic solvents, such as lower aliphatic alcohols or glycol ethers (particularly ethyleneglycol monoethyl ether), optionally containing dissolution aids, such as polyoxyethylene sorbitane monolaurate, monooleate or monostearate (Tween 20 ®, Tween 60 ® or Tween 80 ®). The injectable solutions may contain various other additives, such as preserving agents (e.g. benzyl alcohol, methyl or propyl-p-hydroxybenzoate, phenylmercuric borate or benzalkonium chloride), antioxidants (e.g. sodium pyrosulfate, ascorbic acid, tocoferol, etc.), complexing agents for binding traces of heavy metals (e.g. ethylenediamine tetraacetate), substances for adjusting the pH, buffers, and optionally local anaesthetic agents (e.g. lidocaine).

The injectable solutions are filtered, filled into vials, the vials are closed and sterilized.

The desirable dosage unit for administration includes 15 to 60 mg of indomethacin and 150 to 1000 mg of one or more salicylates. The typical combined daily dosage for human use is 150 to 250 mg of indomethacin and 1500 to 2500 mg of salicylate.

The invention is elucidated in detail by the aid of the following Examples.

EXAMPLE 1

Film-coated tablets containing indomethacin and Na-salicylate as active agents

| Composition of one tablet: | |
|---|---|
| indomethacin | 20 mg |
| Na-salicylate | 200 mg |
| magnesium stearate | 3 mg |
| polyvinylpyrrolidone | 8 mg |
| Eudragit-L$^R$ | 10 mg |
| talc | 12 mg |
| potato starch | 157 mg |
| total | 410 mg |

The tablets are prepared by the conventional wet granulation-compression technique, and film-coated with Eudragit-L ®.

In the above composition Na-salicylate can be replaced by another alkali salicylate, such as lithium salicylate to obtain tablets with the same effect.

EXAMPLE 2

Suppositories containing indomethacin and Na-salicylate as active agents

| Composition of one suppository: | |
|---|---|
| indomethacin | 0.02 g |
| Na-salicylate | 0.20 g |
| Witepsol H-15$^R$ | 1.78 g |
| total | 2.00 g |

The above components are admixed with each other and the mixture is cast into suppository molds.

In the above composition Na-salicylate can be replaced by lithium salicylate.

We claim:

1. A method of attenuating the ulcerogenic effect of indomethacin upon an ulcer-prone subject which comprises orally administering the indomethacin, in a pharmaceutically effective amount, in combination with 7.5 to 25 parts by weight of salicylic acid or an alkali salicylate calculated for one part by weight of the indomethacin.

2. The method defined in claim 1 wherein the indomethacin is administered in a dosage unit of 15 to 60 mg.

3. The method defined in claim 2 wherein about 10 parts by weight of the salicylic acid or alkali metal salicylate is combined with one part by weight of indomethacin.

4. The method defined in claim 1 which comprises administering the indomethacin in a pharmaceutically effective amount in combination with 10 to 20 parts by weight of salicyclic acid or an alkali salicylate calculated for 1 part by weight of the indomethacin.

5. The method defined in claim 4 which comprises administering the indomethacin in a pharmaceutically effective amount in combination with about 10 parts by weight of salicylic acid or alkali salicylate calculated for 1 part by weight of the indomethacin.

6. The method defined in claim 4 which comprises administering the indomethacin in a pharmaceutically effective amount in combination with about 20 parts by weight of salicyclic acid or alkali salicylate calculated for 1 part by weight of the indomethacin.

7. A pharmaceutical composition comprising an effective amount of indomethacin and about 10 parts by weight of salicylic acid or alkali metal salicylate combined with one part by weight of the indomethacin.

8. The composition defined in claim 7 wherein the indomethacin is combined with Na-salicylate.

9. An antiphlogistic method of treating a subject susceptible to ulcerogenesis upon treatment with indomethacin, which comprises administering over an extended period of antiinflammatory dosage of indomethacin combined with an alkali metal salicylate, the alkali metal salicylate being present in an amount of about 10 parts by weight per parts by weight of indomethacin, the dosage of indomethacin being sufficient over said extended period to induce ulcers in said subject in the absence of the alkali metal salicylate.

10. The method defined in claim 9 wherein the dosage of indomethacin is administered in dosage units of 15 to 60 mg.

11. The method defined in claim 10 wherein the alkali metal salicylate is Na-salicylate.

* * * * *